(12) United States Patent
Yasuda et al.

(10) Patent No.: US 9,080,913 B2
(45) Date of Patent: Jul. 14, 2015

(54) TERAHERTZ-WAVE SPECTROMETER AND PRISM MEMBER

(75) Inventors: Takashi Yasuda, Hamamatsu (JP);
Yoichi Kawada, Hamamatsu (JP);
Atsushi Nakanishi, Hamamatsu (JP);
Kouichiro Akiyama, Hamamatsu (JP);
Hironori Takahashi, Hamamatsu (JP)

(73) Assignee: HAMAMATSU PHOTONICS K.K, Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/005,849

(22) PCT Filed: Feb. 21, 2012

(86) PCT No.: PCT/JP2012/054157
§ 371 (c)(1),
(2), (4) Date: Sep. 18, 2013

(87) PCT Pub. No.: WO2012/132645
PCT Pub. Date: Oct. 4, 2012

(65) Prior Publication Data
US 2014/0008540 A1    Jan. 9, 2014

(30) Foreign Application Priority Data
Mar. 29, 2011    (JP) .................................. 2011-072414

(51) Int. Cl.
*G01J 5/02*    (2006.01)
*G01J 3/42*    (2006.01)
(Continued)

(52) U.S. Cl.
CPC ................. *G01J 3/42* (2013.01); *G01J 3/0205* (2013.01); *G01N 21/3581* (2013.01); *G01N 21/552* (2013.01)

(58) Field of Classification Search
USPC .............................. 250/339.01–339.15, 339.1
See application file for complete search history.

(56) References Cited

U.S. PATENT DOCUMENTS 6,958,853 B1 * 10/2005 Arnone et al. ................ 359/326
2002/0067480 A1   6/2002 Takahashi
(Continued)

FOREIGN PATENT DOCUMENTS

DE          3715 481 A1    11/1988
EP          1 630 542       3/2006
(Continued)

OTHER PUBLICATIONS

International Search Report dated Jun. 5, 2012 issued in International Application No. PCT/JP2012/054159.
(Continued)

*Primary Examiner* — David J Makiya
*Assistant Examiner* — Taeho Jo
(74) *Attorney, Agent, or Firm* — Drinker Biddle & Reath LLP

(57) ABSTRACT

By mating a main part with a first prism part or second prism part, a terahertz-wave spectrometer can easily switch between optical paths of a terahertz wave T propagating within a spectroscopic prism. When the main part mates with the first prism part, the terahertz wave T incident on an entrance surface passes through a depression, so as to be reflected by an arrangement part, whereby reflection spectrometry can be performed. When the main part mates with the second prism part, the terahertz wave T incident on the entrance surface is refracted by the depression, so as to pass through an object to be measured within a groove, whereby transmission spectrometry can be preformed.

6 Claims, 10 Drawing Sheets

(51) Int. Cl.
 *G01N 21/3581* (2014.01)
 *G01J 3/02* (2006.01)
 *G01N 21/552* (2014.01)

(56) References Cited

U.S. PATENT DOCUMENTS

| | | | |
|---|---|---|---|
| 2003/0227668 A1* | 12/2003 | Imai et al. | 359/326 |
| 2004/0114148 A1* | 6/2004 | Agladze et al. | 356/456 |
| 2006/0066942 A1 | 3/2006 | Kouno et al. | |
| 2006/0231762 A1* | 10/2006 | Ohtake et al. | 250/341.8 |
| 2007/0229094 A1 | 10/2007 | Kasai et al. | |
| 2008/0014580 A1* | 1/2008 | Alfano et al. | 435/6 |
| 2008/0239317 A1* | 10/2008 | Schulkin et al. | 356/365 |
| 2008/0259428 A1 | 10/2008 | Zimdars et al. | |
| 2008/0265165 A1* | 10/2008 | Yeh et al. | 250/341.1 |
| 2009/0225312 A1* | 9/2009 | Formanek et al. | 356/326 |
| 2009/0283680 A1* | 11/2009 | Logan et al. | 250/339.07 |
| 2010/0091266 A1* | 4/2010 | Yasuda et al. | 356/51 |
| 2011/0006226 A1* | 1/2011 | Schulkin et al. | 250/493.1 |
| 2011/0057109 A1* | 3/2011 | Guo et al. | 250/340 |
| 2012/0113417 A1* | 5/2012 | Linfield et al. | 356/300 |
| 2014/0008540 A1 | 1/2014 | Yasuda et al. | |
| 2014/0008541 A1 | 1/2014 | Akiyama et al. | |

FOREIGN PATENT DOCUMENTS

| | | |
|---|---|---|
| EP | 1 998 163 A1 | 12/2008 |
| EP | 2 273 254 | 1/2011 |
| JP | S61-232412 | 10/1986 |
| JP | 2000-121551 A | 4/2000 |
| JP | 2004-093495 A | 3/2004 |
| JP | 2006-200931 A | 8/2006 |
| JP | 2007-024540 A | 2/2007 |
| JP | 2007-271361 A | 10/2007 |
| JP | 2007-279025 A | 10/2007 |
| JP | 2008-224449 A | 9/2008 |
| JP | 2008-224451 A | 9/2008 |
| JP | 2008-224452 A | 9/2008 |
| WO | WO-02/18919 A1 | 3/2002 |

OTHER PUBLICATIONS

International Preliminary Report on Patentability dated Oct. 10, 2013 issued in International Application No. PCT/JP2012/054159.
Supplementary European Search Report dated Aug. 18, 2014 issued in European Application No. 12764439.1-1554/2693200 PCT/JP2012054159.
Machine translation of JP 2008-224449 dated Sep. 25, 2008.

* cited by examiner (a)

(b)

(a)

(b)

TERAHERTZ-WAVE SPECTROMETER AND PRISM MEMBER

TECHNICAL FIELD

The present invention relates to a spectrometer and a prism member which use a terahertz wave.

BACKGROUND ART

Conventionally known as an example of techniques relating to a spectrometer using a terahertz wave is a total reflection terahertz-wave spectrometer described in Patent Literature 1. In this total reflection terahertz-wave spectrometer, an entrance surface of an internal total reflection prism is integrally provided with a terahertz-wave generator, while an exit surface of the internal total reflection prism is integrally provided with a terahertz-wave detector. Using such an integral prism integrating the internal total reflection prism, terahertz-wave generator, and terahertz-wave detector together is advantageous in that it can detect the generation of terahertz waves at high efficiency while reducing the size of the total reflection spectrometer.

CITATION LIST

Patent Literature

Patent Literature 1: Japanese Patent Application Laid-Open No. 2008-224449

SUMMARY OF INVENTION

Technical Problem

Meanwhile, the spectrometry using a terahertz wave such as the one mentioned above performs reflection spectrometry which utilizes an interaction between an evanescent wave occurring when the terahertz wave is totally reflected and an object to be measured. On the other hand, as a spectrometric technique, there is also transmission spectrometry which transmits a terahertz wave through the object. These measuring methods have their merits and demerits and thus are selectively employed according to the kind of the object, measurement items, and the like in practice. Therefore, it has also been desired for the spectrometer using a terahertz wave to utilize common structures for reflection spectrometry and transmission spectrometry as much as possible.

For solving the above-mentioned problem, it is an object of the present invention to provide a terahertz-wave spectrometer and a prism member which can easily switch between reflection spectrometry and transmission spectrometry.

Solution to Problem

For achieving the above-mentioned object, the terahertz-wave spectrometer in accordance with the present invention comprises a light source for emitting laser light; a branching unit for splitting the laser light emitted from the light source into pump light and probe light; a terahertz-wave generator for generating a terahertz wave in response to the pump light incident thereon after branching off at the branching unit; a spectroscopic prism, having entrance and exit surfaces for the terahertz wave and an arrangement part for an object to be measured, for propagating therewithin the terahertz wave incident on the entrance surface and emitting the terahertz wave from the exit surface; and a terahertz-wave detector for receiving the terahertz wave emitted from the exit surface of the spectroscopic prism and the probe light branching off at the branching unit and detecting a correlation between the terahertz wave and the probe light; wherein the spectroscopic prism comprises a main part having the entrance and exit surfaces, a depression formed on an upper face side, a first optical surface for collimating or converging the terahertz wave toward the depression, and a second optical surface for converging the terahertz wave having passed through the depression toward the exit surface; a first prism part, formed by a member having a refractive index substantially equal to that of the main part, including a projection adapted to detachably mate with the depression and having an upper face provided with the arrangement part for the object; and a second prism part, formed by a member having a refractive index lower than that of the main part, including a projection adapted to detachably mate with the depression and having a groove to become the arrangement part for the object, the groove being formed from an upper face toward a leading end of the projection; wherein the terahertz wave incident on the entrance surface is transmitted through the depression and reflected by the arrangement part when the first prism part mates with the main part, but is refracted by the depression and transmitted through the groove when the second prism part mates with the main part.

This terahertz-wave spectrometer can easily switch between optical paths of the terahertz wave propagating through the spectroscopic prism as the first or second prism part mates with the main part. When the first prism part mates with the main part, the terahertz wave incident on the entrance surface is transmitted through the depression and reflected by the arrangement part, whereby reflection spectrometry can be performed. When the second prism part mates with the main part, on the other hand, the terahertz wave incident on the entrance surface is refracted by the depression and transmitted through the groove, whereby transmission spectrometry can be performed. The main part is used in common for both measurements, whereby the spectroscopic prism can be kept from becoming complicated.

Preferably, a matching oil is disposed in each of the mating part between the main part and the first prism part and the mating part between the main part and the second prism part. This can prevent the terahertz wave from being multiply reflected at the interface between the main part and the first prism part and the interface between the main part and the second prism part.

Preferably, film members are disposed in the mating part between the main part and the first prism part and the mating part between the main part and the second prism part such as to protrude out thereof. In this case, holding the film members makes it easy to remove the first and second prism parts from the main part.

Preferably, spaces exist in a part of the mating part between the main part and the first prism part and a part of the mating part between the main part and the second prism part. In this case, the existence of spaces makes it easy to remove the first and second prism parts from the main part.

Preferably, the first and second prism parts are provided with lugs. In this case, holding the lugs makes it easy to attach/detach the first and second prism parts to/from the main part.

The prism member in accordance with the present invention is a prism member used in a terahertz-wave spectrometer comprising a light source for emitting laser light; a branching unit for splitting the laser light emitted from the light source into pump light and probe light; a terahertz-wave generator for generating a terahertz wave in response to the pump light incident thereon after branching off at the branching unit; a spectroscopic prism, having entrance and exit surfaces for the terahertz wave and an arrangement part for an object to be measured, for propagating therewithin the terahertz wave incident on the entrance surface and emitting the terahertz wave from the exit surface; and a terahertz-wave detector for detecting a correlation between the terahertz wave and the probe light; the prism member having the entrance and exit surfaces, a depression formed on an upper face side and adapted to detachably mate with another prism member including the arrangement part for the object, and a first optical surface for collimating or converging the terahertz wave toward the arrangement part and a second optical surface for converging the terahertz wave from the arrangement part toward the exit surface when the prism part mates with the depression.

This prism member is formed with a depression adapted to detachably mate with another prism member including an arrangement part for the object. Therefore, mating another prism member having a different property with the depression can easily switch between optical paths for a terahertz wave propagating within the spectroscopic prism. Since the depression is formed on the upper face side, another prism member is easy to attach and detach, and operability in alignment of the terahertz wave can be secured when mating another prism member with the depression.

Advantageous Effects of Invention

The present invention can easily switch between reflection spectrometry and transmission spectrometry.

DESCRIPTION OF EMBODIMENTS

In the following, preferred embodiments of the terahertz-wave spectrometer in accordance with the present invention will be explained in detail with reference to the drawings.

Figure 1:
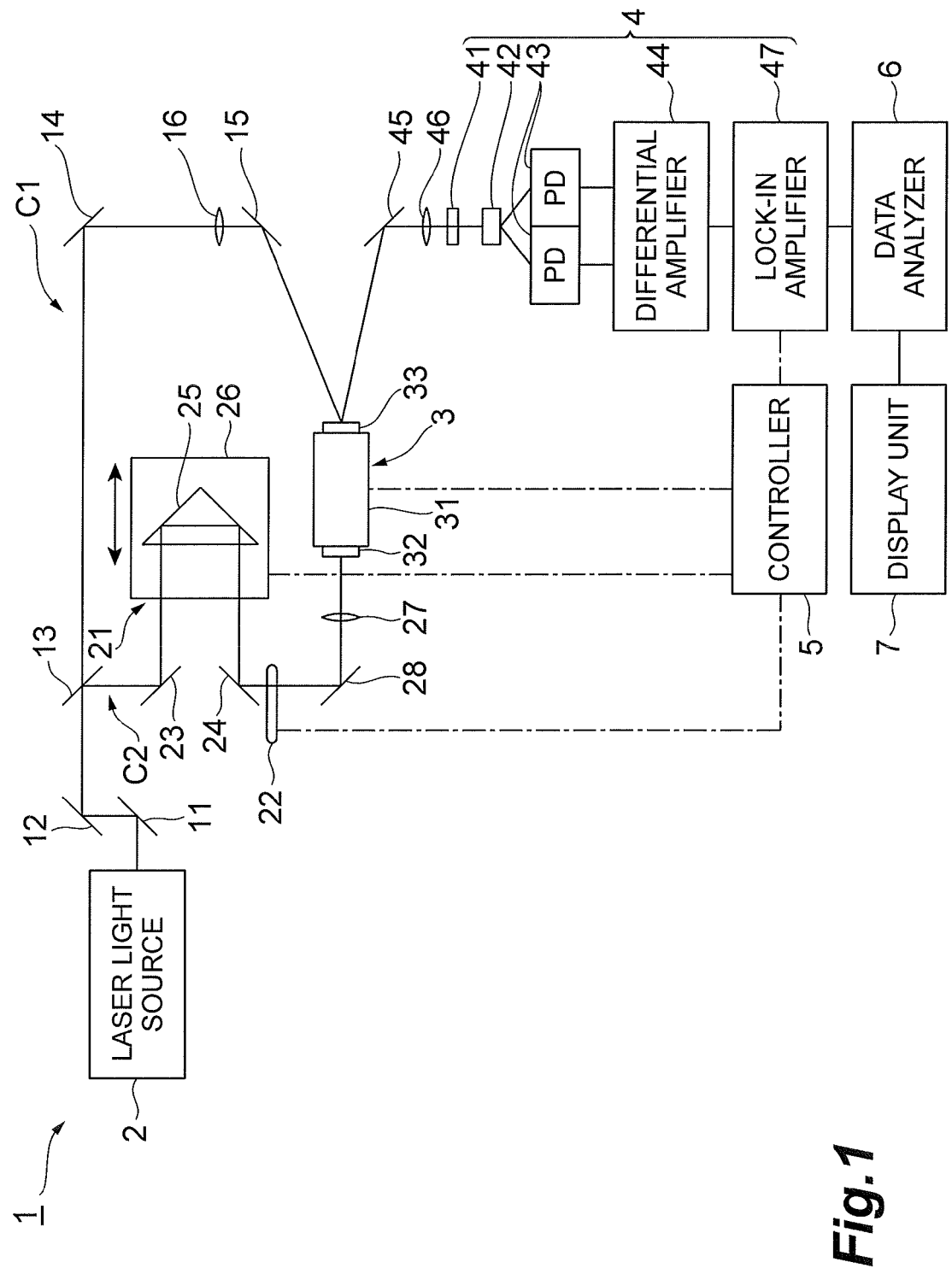
FIG. 1 is a diagram illustrating an embodiment of the terahertz-wave spectrometer in accordance with the present invention.

FIG. 1 is a diagram illustrating an embodiment of the terahertz-wave spectrometer in accordance with the present invention. As illustrated in the drawing, this terahertz-wave spectrometer 1 comprises a laser light source 2 for emitting laser light, an integral prism 3 in which a terahertz-wave generator 32, a spectroscopic prism 31, and a terahertz-wave detector 33 are integrated together, and a detection unit 4 for detecting a terahertz wave. The terahertz-wave spectrometer 1 also comprises a controller 5 for controlling operations of the constituents mentioned above, a data analyzer 6 for analyzing data according to an output from the detection unit 4, and a display unit 7 for displaying results of processing in the data analyzer 6.

The laser light source 2 is a light source for generating a femtosecond pulsed laser. The laser light source 2 issues a femtosecond pulsed laser having an average power of 120 mW and a repetition rate of 77 MHz, for example. The femtosecond pulsed laser emitted from the laser light source 2 impinges on mirrors 11, 12 in sequence and then is split into two, i.e., pump light 48 and probe light 49, by a beam splitter 13. A probe light optical path C1 through which the probe light 49 propagates is provided with mirrors 14, 15 and a lens 16, so that the probe light 49 is converged by the lens 16, so as to be made incident on a terahertz-wave detector 33 which will be explained later.

On the other hand, a pump light optical path C2 through which the pump light 48 propagates is provided with a delay unit 21 and a modulator 22. The delay unit 21, which is constructed by a pair of mirrors 23, 24 and a reflection prism 25 disposed on a movable stage 26, can adjust a delay in the pump light 48 by moving the position of the reflection prism 25 back and forth with respect to the pair of mirrors 23, 24. The modulator 22 is a part which switches between transmitting and blocking the pump light 48 by an optical chopper, for example. According to a signal from the controller 5, the modulator 22 modulates the switching between transmitting and blocking the pump light 48 at 1 kHz, for example.

Figure 2:
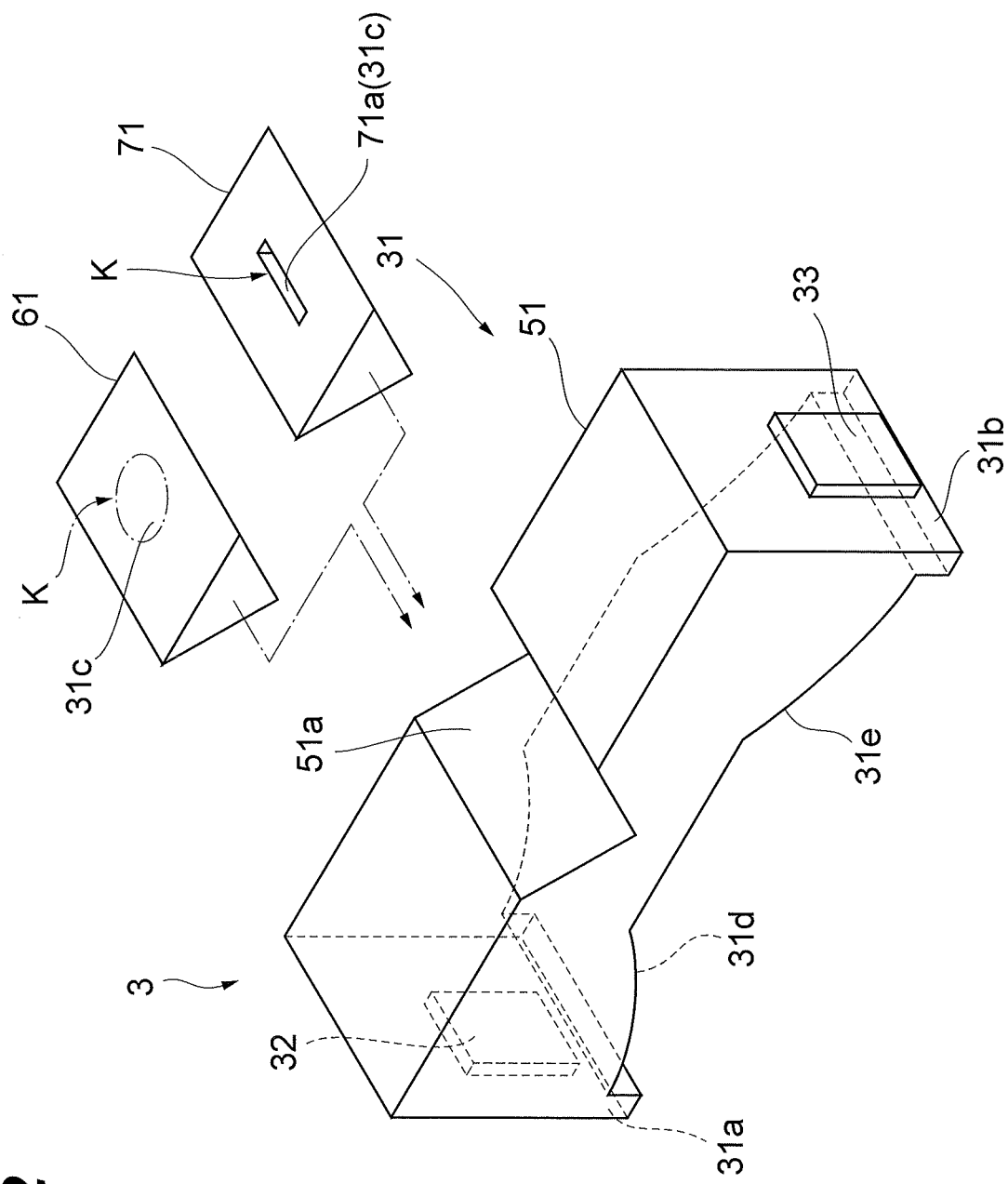
FIG. 2 is a perspective view of an integral prism used in the terahertz-wave spectrometer illustrated in FIG. 1.
Figure 3:
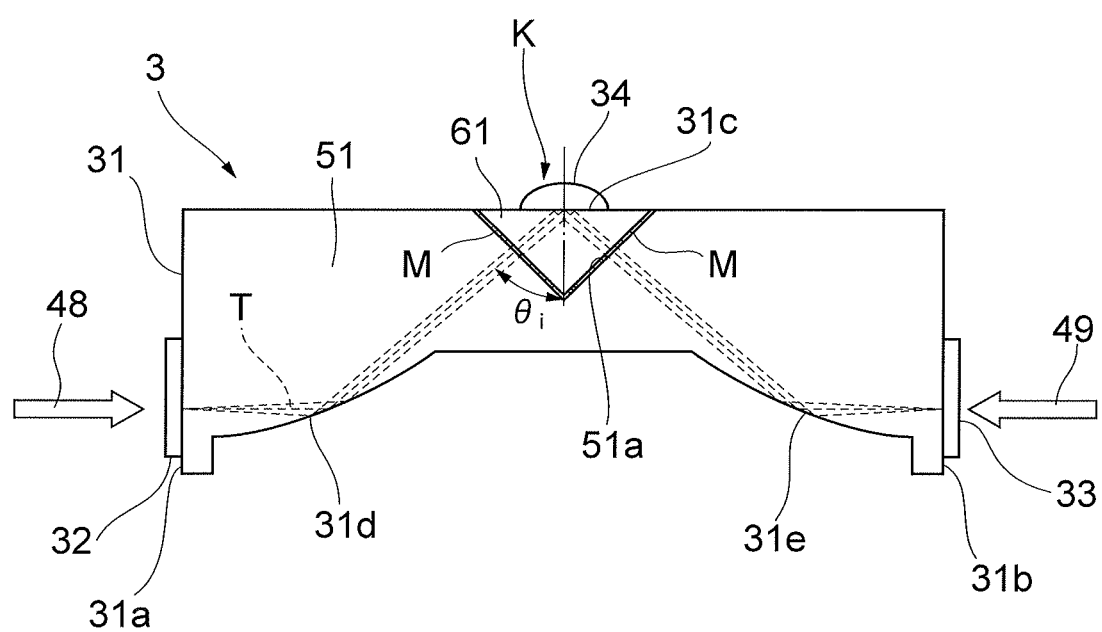
FIG. 3 is a side view of the integral prism when mating with a first prism part.

The pump light 48 propagated through the pump light optical path C2 impinges on a mirror 28 and then is converged by a lens 27, so as to be made incident on the integral prism 3. As illustrated in FIGS. 2 and 3, the spectroscopic prism 31 constituting the integral prism 3, which is formed by Si, for example, has an entrance surface 31a to which the terahertz-wave generator 32 is integrally secured and an exit surface 31b to which the terahertz-wave detector 33 is integrally secured. The upper face of the spectroscopic prism 31 forms an arrangement part 31c to be arranged with an object to be measured 34, from which various optical constants such as refractive index, dielectric constant, and absorption coefficient are measured, and an arrangement region K is set therein.

Figure 4:
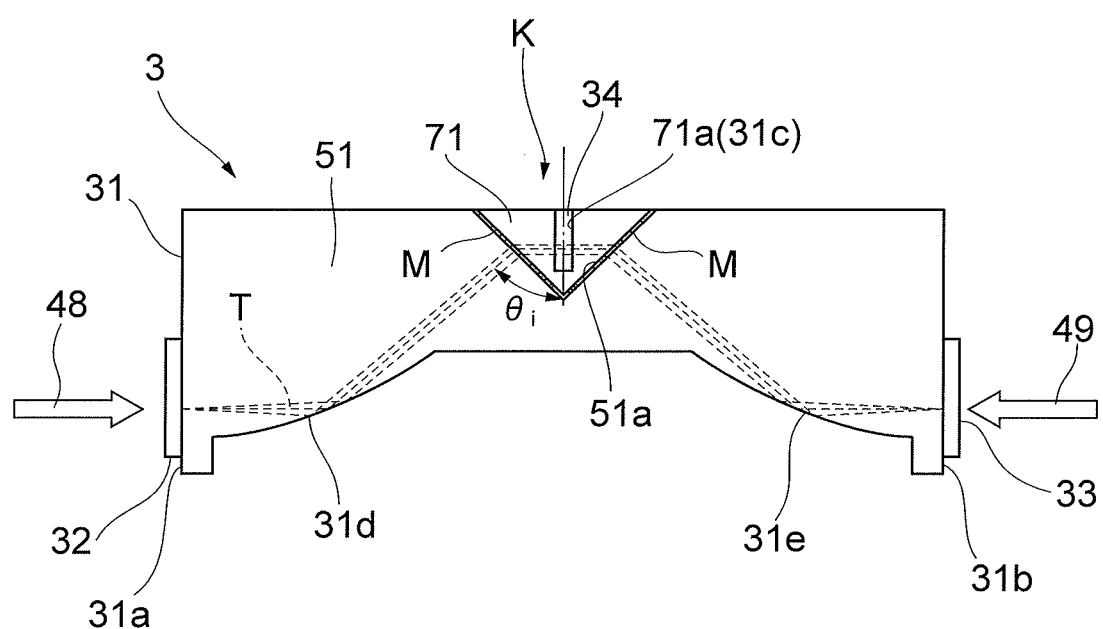
FIG. 4 is a side view of the integral prism when mating with a second prism part.

In the bottom face of the spectroscopic prism 31, as illustrated in FIGS. 3 and 4, a first optical surface 31d for collimating the terahertz wave T generated in the terahertz-wave generator 32 toward the arrangement part 31c is provided between the entrance surface 31a and the arrangement part 31c. A second optical surface 31e for converging the terahertz wave T from the arrangement part 31c toward the exit surface 31b is provided between the arrangement part 31c and the exit surface 31b. The first and second optical surfaces 31d, 31e are formed by curving the bottom face of the spectroscopic prism 31 into a predetermined form.

Nonlinear optical crystals of ZnTe and the like, antenna elements such as optical switches using GaAs, semiconductors such as InAs, and superconductors, for example, can be used as the terahertz-wave generator 32. The pulse of the terahertz wave T generated from these elements is in the order of several picoseconds in general. When a nonlinear optical crystal is used as the terahertz-wave generator 32, the pump light 48 incident on the terahertz-wave generator 32, if any, is converted into the terahertz wave T by a nonlinear optical effect.

Electrooptical crystals of ZnTe and the like and antenna elements such as optical switches using GaAs, for example, can be used as the terahertz-wave detector 33. When the terahertz wave T and the probe light 49 are incident on the terahertz-wave detector 33 at the same time in the case where an electrooptical crystal is used as the terahertz-wave detector 33, the probe light 49 incurs birefringence due to the Pockels effect. The amount of birefringence in the probe light 49 is in proportion to the electric field intensity of the terahertz wave T. Therefore, detecting the amount of birefringence of the probe light 49 makes it possible to sense the terahertz wave T.

For example, a thermosetting adhesive is used for securing the terahertz-wave generator 32 and the terahertz-wave detector 33. Preferably, the adhesive used here is transparent at the wavelength of the terahertz wave T and has a refractive index in the middle between or equivalent to each of the respective refractive indexes of the terahertz-wave generator 32 and terahertz-wave detector 33 and the refractive index of the spectroscopic prism 31.

A wax transparent at the wavelength of the terahertz wave T may be melted and coagulated in place of the adhesive, or marginal parts of the terahertz-wave generator 32 and terahertz-wave detector 33 may be secured with the adhesive while the terahertz-wave generator 32 and terahertz-wave detector 33 are in direct contact with the entrance surface 31a and exit surface 31b, respectively.

When the terahertz-wave detector 33 is an electrooptical crystal, the detection unit 4 for detecting the terahertz wave is constituted by a quarter wave plate 41, a polarizer 42, a pair of photodiodes 43, 43, a differential amplifier 44, and a lock-in amplifier 47, for example, as illustrated in FIG. 1. The probe light 49 reflected by the terahertz-wave detector 33 is guided by the mirror 45 toward the detection unit 4, converged by a lens 46, so as to be transmitted through the quarter wave plate 41, and then separated by the polarizer 42, which is a Wollaston prism or the like, into vertical and horizontal linearly polarized light components. The vertical and horizontal linearly polarized light components are converted into their respective electric signals by the pair of photodiodes 43, 43, while the difference therebetween is detected by the differential amplifier 44. The output signal from the differential amplifier 44 is amplified by the lock-in amplifier 47 and then fed to the data analyzer 6.

The differential amplifier 44 outputs a signal having an intensity in proportion to the electric field intensity of the terahertz wave T when the terahertz wave T and the probe light 49 are incident on the terahertz-wave detector 33 at the same time, but no signal when not.

In the reflection spectrometry, an evanescent wave emitted when the terahertz wave T is reflected by the arrangement part 31c of the spectroscopic prism 31 interacts with the object 34 arranged on the arrangement part 31c of the spectroscopic prism 31, thereby changing the reflectance of the terahertz wave T from that in the case where the object 34 is not in place. Therefore, measuring the change in reflectance of the terahertz wave T can evaluate the spectroscopic characteristic of the object 34.

In the transmission spectrometry, on the other hand, information concerning optical constants of the object 34 arranged on the arrangement part 31c is acquired when the terahertz wave T passes through the object 34. Therefore, measuring the information included in the terahertz wave T can evaluate the spectroscopic characteristic of the object 34.

The data analyzer 6 is a part which performs data analysis processing of spectrometry according to an analysis program exclusively used by the terahertz-wave spectrometer 1, for example, and is physically a computer system having a CPU (central processing unit), a memory, an input device, the display unit 7, and the like. The data analyzer 6 executes data analysis processing according to a signal fed from the lock-in amplifier 47 and causes the display unit 7 to display results of analysis.

Figure 6:
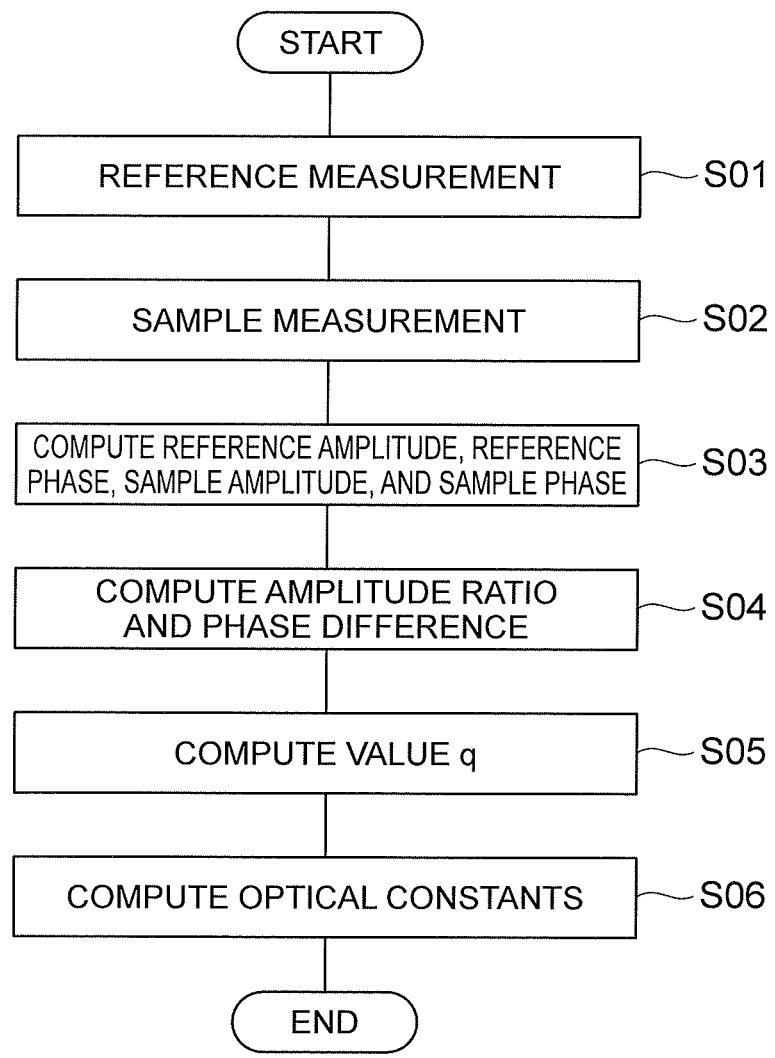
FIG. 6 is a flowchart illustrating a procedure of deriving optical constants of an object to be measured in reflection spectrometry.

FIG. 6 is a flowchart illustrating a procedure of deriving optical constants of the object 34 in reflection spectrometry. The following explanation will assume a case where the terahertz wave T is incident as p-polarized light on the reflecting part 31c of the spectroscopic prism 31.

First, as illustrated in FIG. 6, the terahertz-wave spectrometer is used for performing reference measurement and sample measurement (steps S01 and S02). The reference measurement measures a material (e.g., air) having known optical constants, while the sample measurement measures a material from which optical constants are to be obtained. Subsequently, a reference measurement result $T_{ref}$ and a sample measurement result $T_{sig}$ are respectively Fourier-transformed, so as to determine a reference amplitude $R_{ref}$, a reference phase $\Phi_{ref}$, a sample amplitude $R_{sig}$, and a sample phase $\Phi_{sig}$ (step S03).

Next, the ratio P between the reference amplitude $R_{ref}$ and sample amplitude $R_{sig}$ is determined according to expression (1), and the phase difference $\Delta$ between the reference phase $\Phi_{ref}$ and sample phase $\Phi_{sig}$ is determined according to expression (2) (step S04).

[Math. 1]
$$P = \left|\frac{R_{sig}}{R_{ref}}\right| \quad (1)$$

[Math. 2]
$$\Delta = \Phi_{sig} - \Phi_{ref} \quad (2)$$

Further, using the above-mentioned ratio P and phase difference $\Delta$, a value q is defined as in expression (3) (step S05).

[Math. 3]
$$q = \frac{1 - Pe^{-i\Delta}}{1 + Pe^{-i\Delta}} \quad (3)$$

Here, let $\theta_i$ (see FIG. 3) be the angle at which the terahertz wave T is incident on the spectroscopic prism 31, and $\theta_{ref}$ and $\theta_{sig}$ be the respective refraction angles determined by Snell's law in the reference measurement and sample measurement. Further, using the Fresnel equations of reflection, $Pe^{-i\Delta}$ in the expression (3) can be represented by the following expression (4):

[Math. 4]
$$Pe^{-i\Delta} = \frac{\tan(\theta_i - \theta_{sig})}{\tan(\theta_i + \theta_{sig})} \cdot \frac{\tan(\theta_i + \theta_{ref})}{\tan(\theta_i - \theta_{ref})} \quad (4)$$

Substituting the above-mentioned expression (4) into the expression (3) and modifying it yields the following expression (5):

[Math. 5]

$$\sin\theta_{sig} \cdot \cos\theta_{sig} = \frac{q \cdot \sin^2\theta_i \cos^2\theta_i + \sin\theta_i \cos\theta_i \sin\theta_{ref} \cos\theta_{ref}}{\sin\theta_i \cos\theta_i + q \cdot \sin\theta_{ref} \cos\theta_{ref}} \quad (5)$$

Letting $n_{prism}$ be the complex refractive index of the material constituting the spectroscopic prism 31, and $n_{sample}$ be the complex refractive index of the object 34, the Snell's law is as in the following expression (6), while the square of the complex refractive index of the object 34 is represented by expression (7). Therefore, substituting the expression (5) into the expression (7) can determine the complex refractive index of the object 34, thereby deriving desirable optical constants of the object 34 (step S06).

[Math. 6]

$$n_{prism}\sin\theta_i = n_{sample}\sin\theta_{sig} \quad (6)$$

[Math. 7]

$$n_{sample}^2 = \frac{\sin^2\theta_i \cdot \left(1 - \sqrt{1 - 4 \cdot (\sin\theta_{sig} \cdot \cos\theta_{sig})^2}\right)}{2 \cdot (\sin\theta_{sig} \cdot \cos\theta_{sig})^2} \cdot n_{prism}^2 \quad (7)$$

Figure 7:
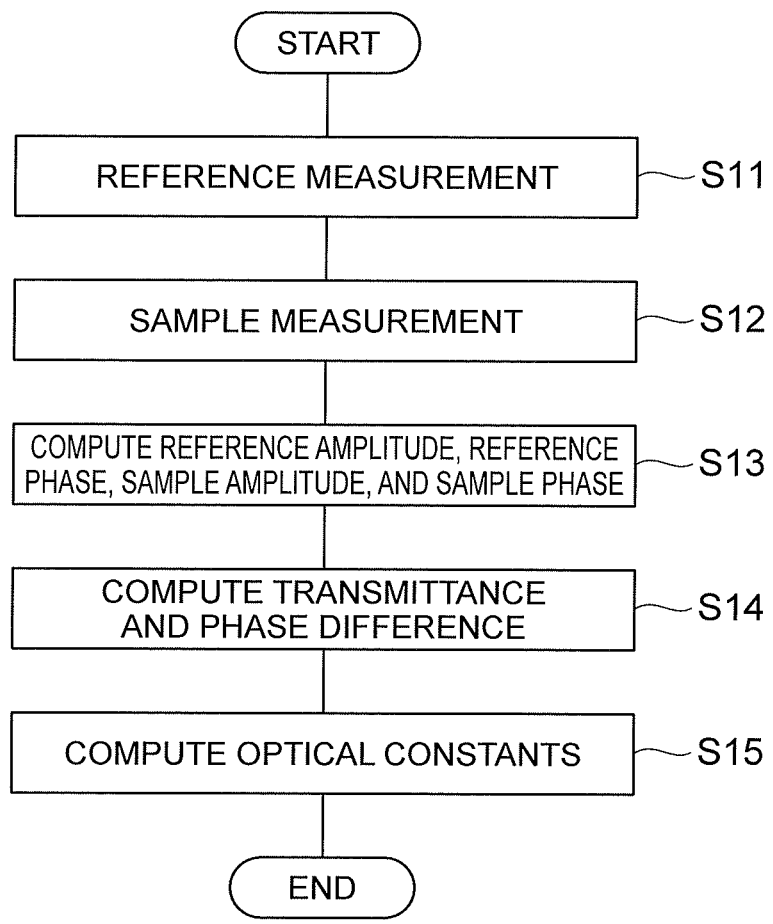
FIG. 7 is a flowchart illustrating a procedure of deriving optical constants of the object in transmission spectrometry.

On the other hand, FIG. 7 is a flowchart illustrating a procedure of deriving optical constants of the object in transmission spectrometry (see OYO BUTURI, Vol. 75, No. 2 (2006), p. 179 for this procedure).

As illustrated in FIG. 7, the terahertz-wave spectrometer 1 is initially used for performing reference measurement and sample measurement in transmission spectrometry (steps S11 and S12) as well. The reference measurement measures a material (e.g., air) having known optical constants, while the sample measurement measures a material from which optical constants are to be obtained. Subsequently, a reference measurement result $T_{ref}$ and a sample measurement result $T_{sig}$ are respectively Fourier-transformed, so as to determine a reference amplitude $R_{ref}$, a reference phase $\Phi_{ref}$, a sample amplitude $R_{sig}$, and a sample phase $\Phi_{sig}$ (step S13).

Next, a transmittance T is determined by expression (8) according to the reference amplitude $R_{ref}$ and sample amplitude $R_{sig}$, and a phase difference $\Delta$ between the reference phase $\Phi_{ref}$ and sample phase $\Phi_{sig}$ is determined by expression (9) (step S14).

[Math. 8]

$$T = \left|\frac{R_{sig}}{R_{ref}}\right|^2 \quad (8)$$

[Math. 9]

$$\Delta = \Phi_{sig} - \Phi_{ref} \quad (9)$$

These values are represented as expression (11) by using the complex refractive index of the object (expression (10)). Here, $t_{as}$ and $t_{sa}$, which are Fresnel reflection coefficients, in the expression (11) are represented as in expressions (12) and (13), respectively.

[Math. 10]

$$\tilde{n} = n + i\kappa \quad (10)$$

[Math. 11]

$$\tilde{t}(\omega) \equiv \sqrt{T(\omega)} \exp(i\Delta\phi(\omega)) = t_{as} \cdot t_{sa} \cdot \exp\left\{i\frac{(\tilde{n}(\omega) - i)d\omega}{c}\right\} \quad (11)$$

[Math. 12]

$$t_{as} = 2/\tilde{n} + 1 \quad (12)$$

[Math. 13]

$$t_{sa} = 2\tilde{n}/\tilde{n} + 1 \quad (13)$$

These allow the complex refractive index of the object 34 to be determined from simultaneous equations of the following expressions (14) and (15), so as to derive desirable optical constants of the object 34 (step S15).

[Math. 14]

$$n(\omega) = \frac{c}{d\omega}\left[\Delta\phi(\omega) + \frac{d\omega}{c} - \arg(t_{as} \cdot t_{sa})\right] \quad (14)$$

[Math. 15]

$$\kappa(\omega) = -\frac{c}{2d\omega}\ln\left[\frac{T(\omega)}{|t_{as} \cdot t_{sa}|^2}\right] = -\frac{c}{2d\omega}\ln\left[\frac{T(\omega)}{|1 - r_{as}^2|^2}\right] \quad (15)$$

The structure of the above-mentioned integral prism 3 will now be explained in further detail.

As illustrated in FIG. 2, the integral prism 3 exhibits a function as the spectroscopic prism 31 by combining the main part 51 with one of first and second prism parts 61, 71. The main part 51 includes the above-mentioned entrance surface 31a, exit surface 31b, first optical surface 31d, and second optical surface 31e. A groove 51a having a triangular cross section extending in a direction intersecting an optical path of the terahertz wave T within the integral prism 3 when the main part 51 is seen from the upper face side is formed on the upper face side of the main part 51.

The first prism part 61 is formed into a triangular cross section having the same length as with the groove 51a of the main part 51 by Si as with the main part 51, for example. The bottom face side of the first prism part 61 is formed into a projection adapted to mate with the groove 51a of the main part 51. The upper face of the first prism part 61 is provided with the arrangement part 31c to be arranged with the object 34.

The second prism part 71 is formed into a triangular cross section having the same length as with the groove 51a of the main part 51 by a member having a refractive index lower than that of the main part (e.g., a plastic having a refractive index of about 1.5), for example. The bottom face side of the second prism part 71 is formed into a projection adapted to mate with the groove 51a of the main part 51. A groove 71a having a rectangular cross section is formed on the upper face of the second prism part 71 so as to be directed from the upper face toward the leading end of the projection. The groove 71a serves as the arrangement part 31c to be arranged with the object 34.

When the first prism part 61 mates with the main part 51, as illustrated in FIG. 3, the terahertz wave T entering the spectroscopic prism 31 from the entrance surface 31a is reflected by the first optical surface 31d to the depression 51a and then passes through the mating part between the main part 51 and the first prism part 61, so as to be totally reflected by the arrangement part 31c arranged with the object 34. The terahertz wave T totally reflected by the arrangement part 31c passes through the mating part between the main part 51 and the first prism part 61 and then is reflected by the second optical surface 31e, so as to exit from the exit surface 31b.

When the second prism part 71 mates with the main part 51, on the other hand, as illustrated in FIG. 4, the terahertz wave T entering the spectroscopic prism 31 from the entrance surface 31a is reflected by the first optical surface 31d to the depression 51a and then refracted by the mating part between the main part 51 and the second prism part 71, so as to pass through the object 34 within the groove 71a. The terahertz wave T transmitted through the object 34 is refracted by the mating part between the main part 51 and the second prism part 71 and then reflected by the second optical surface 31e, so as to exit from the exit surface 31b.

Figure 5:
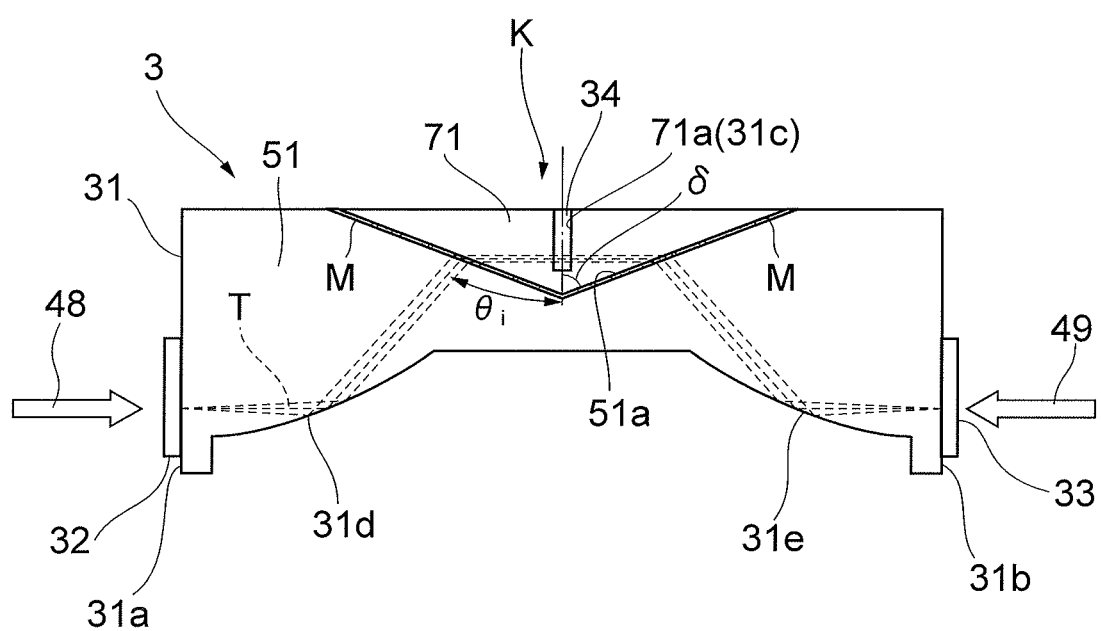
FIG. 5 is a side view of the integral prism when mating with a second prism part having a different form.

When the incidence angle θi of the terahertz wave T with respect to the spectroscopic prism 31 is 45° in the case where the spectroscopic prism 31 is made of Si having a refractive index of 3.4 while the second prism part 71 is made of a plastic having a refractive index of 1.5, for example, the opening angle δ of the groove 51a having the triangular cross section may be 69° as illustrated in FIG. 5. Here, the terahertz wave T is refracted by the mating part between the main part 51 and the second prism part 71, so as to be substantially perpendicularly incident on the object 34 within the groove 71a. The terahertz wave T transmitted through the object 34 is refracted by the mating part between the main part 51 and the second prism part 71, so as to return to the same path as in the case of mating with the first prism part 61, and is reflected by the second optical surface 31e, so as to exit from the exit surface 31b. Here, a tolerance of about ±1° is permitted.

Preferably, a matching oil M is disposed in the mating part between the main part 51 and the first prism part 61 and the mating part between the main part 51 and the second prism part 71 so as to correspond to an optical path region where the terahertz wave T passes. This can prevent the terahertz wave T from being multiply reflected by the interface between the main part 51 and the first prism part 61 and the interface between the main part 51 and the second prism part 71.

As explained in the foregoing, by mating the main part 51 with the first prism part 61 or second prism part, the terahertz-wave spectrometer 1 can easily switch between optical paths of the terahertz wave T propagating within the spectroscopic prism 31. When the main part 51 mates with the first prism part 61, the terahertz wave T incident on the entrance surface 31a passes through the depression 51a, so as to be reflected by the arrangement part 31c, whereby reflection spectrometry can be performed. When the main part 51 mates with the second prism part 71, on the other hand, the terahertz wave T incident on the entrance surface 31a is refracted by the depression 51a, so as to pass through the object 34 within the groove 71a, whereby transmission spectrometry can be preformed. The main part 51 is used in common for both measurements, whereby the spectroscopic prism 31 can be kept from becoming complicated.

The upper face of the main part 51 is formed with the depression 51a in this embodiment. This makes it easy to attach and detach the first and second prism parts 61, 71 and secures operability in alignment of the terahertz wave T when mating the first and second prism parts 61, 71 with the depression 51a.

The present invention is not limited to the above-mentioned embodiment.

For example, while each of the first and second prism parts 61, 71 and the depression 71 has a triangular cross section in the above-mentioned embodiment, other forms such as a rectangular cross section may also be employed. The mating parts are not limited to flat surfaces but may be curved surfaces. When the mating part is a curved surface, which is not depicted, it is preferable for the form of the curved surface to be adjusted such that the terahertz wave T refracted by the mating part between the main part 51 and the second prism part 71 when the main part 51 mates with the second prism part 71 passes through the object 34 as parallel light. The curved surface form may also be adjusted such that the terahertz wave T refracted by the mating part between the main part 51 and the second prism part 71 is converged toward the object 34. The length of each of the first and second prism parts 61, 71 may be either longer or shorter than that of the groove 51a of the main part 51 without being restricted to the same length as therewith.

Figure 8:
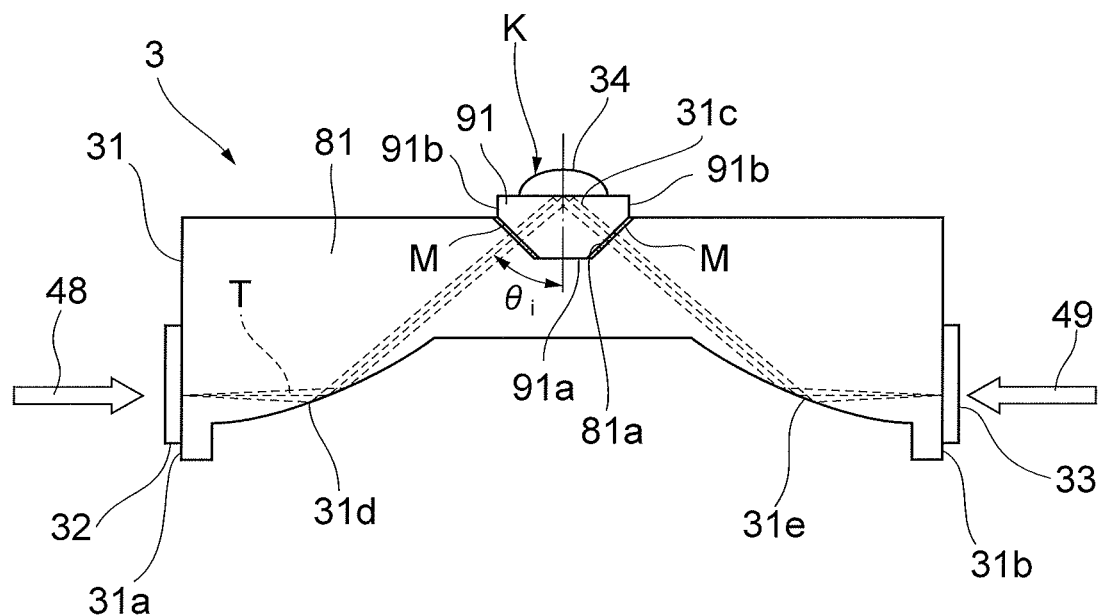
FIG. 8 is a set of diagrams illustrating a modified example of the first and second prism parts.
Figure 8:
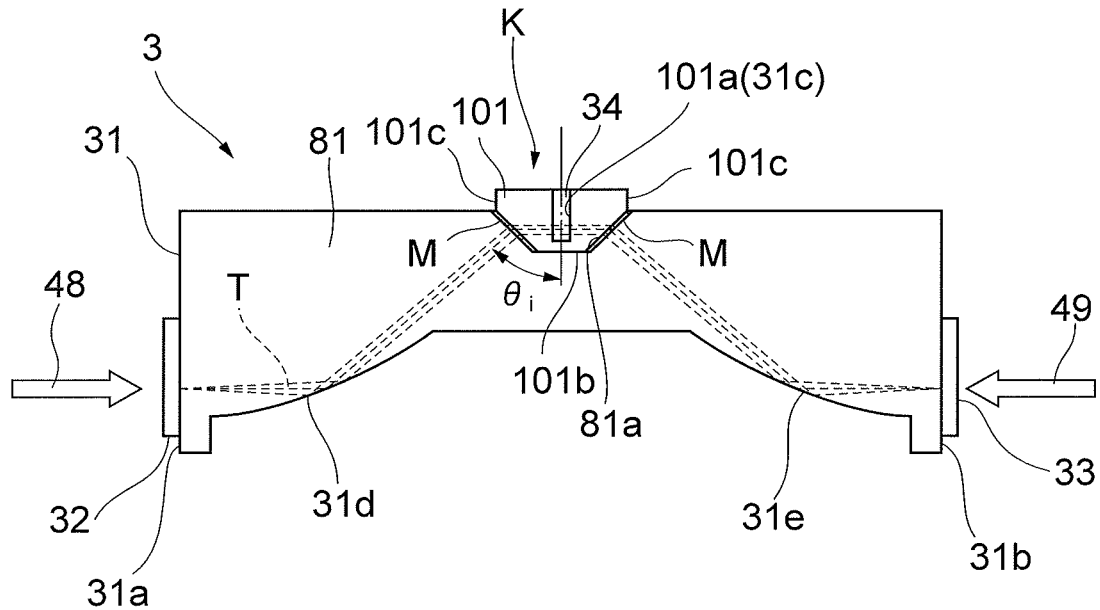

A modified example of the prism part may be constructed as illustrated in FIG. 8(a) such that the bottom face of a first prism part 91 is formed with a flat surface 91a parallel to the upper face thereof, while both side parts are formed with side faces 91b, 91b orthogonal to the upper face. Similarly, as illustrated in FIG. 8(b), for example, the bottom face of a second prism part 101 may be formed with a flat surface 101b parallel to the upper face thereof with both side parts being formed with side faces 101c, 101c orthogonal to the upper face.

In this case, a main part 81 is provided with a groove 81a conforming to the form of the first and second prism parts 91, 101. Preferably, the upper face of the main part 81 is made lower than that in the case of FIGS. 3 and 4, so that the side faces 91b, 91b and 101c, 101c project from the upper face of the main part 81 when the first and second prism parts 91, 101 mate with the depression 81a of the main part 81. This enables the side faces 91b, 91b and 101c, 101c to function as lugs for the first and second prism parts 91, 101, thereby making it easy to attach/detach the first and second prism parts 91, 101 to/from the main part 81.

Figure 9:
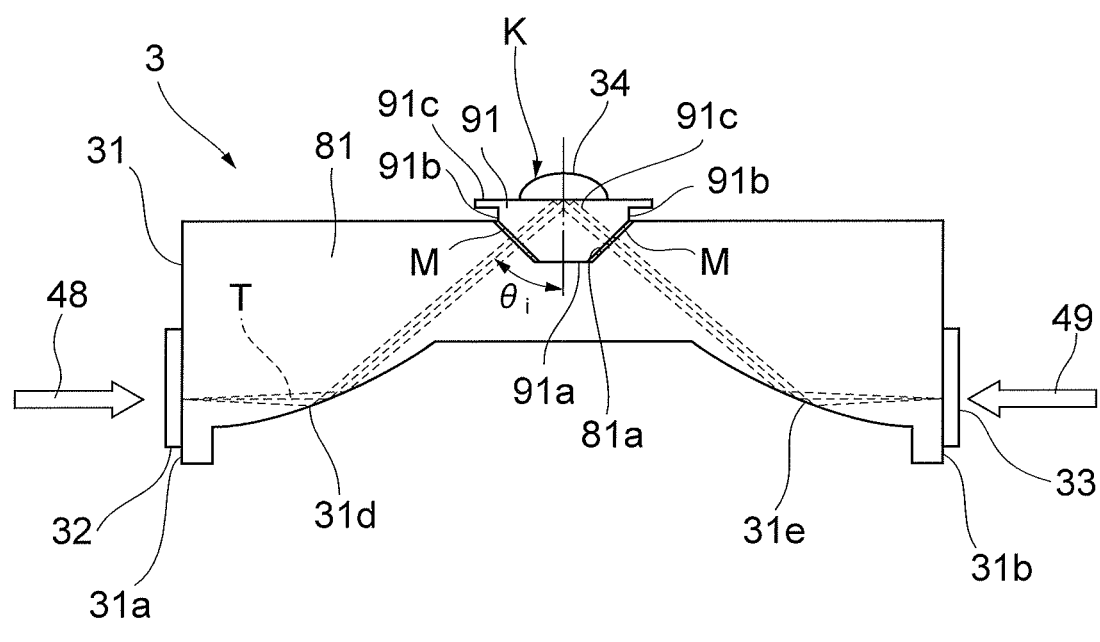
FIG. 9 is a set of diagrams illustrating another modified example of the first and second prism parts.
Figure 9:
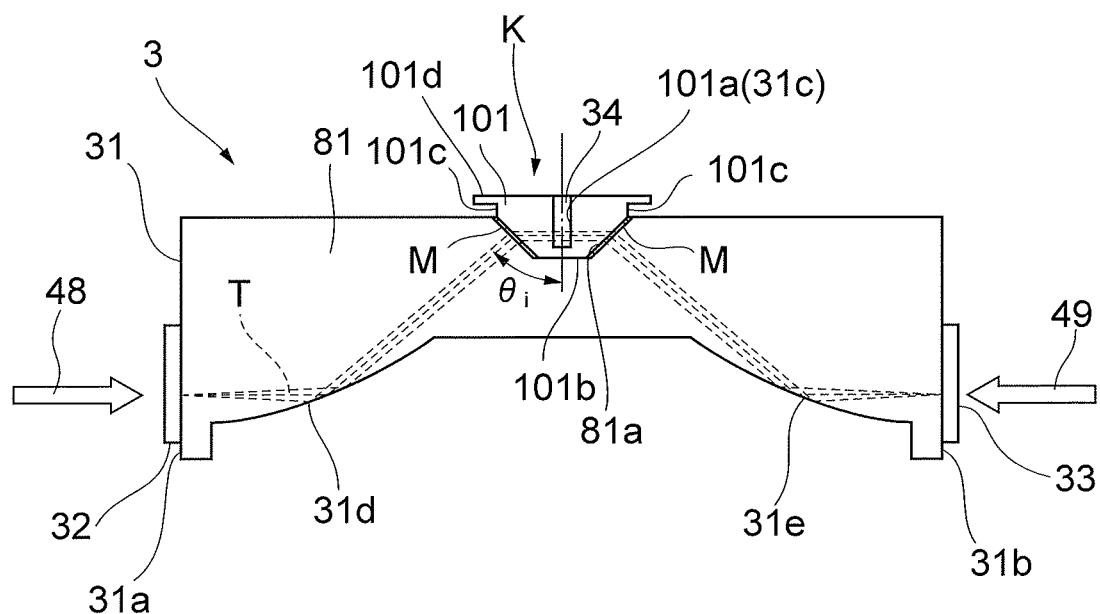

For example, the first prism part 91 may further be provided with lugs 91c, 91c projecting like plates from the side faces 91b, 91b as illustrated in FIG. 9(a), while the second prism part 101 may further be provided with lugs 101c, 101c projecting like plates from the side faces 101b, 101b as illustrated in FIG. 9(b). This makes it easier to handle the first and second prism parts 91, 101. The positions of the lugs are not restricted in particular as long as they do not inhibit the terahertz wave T from propagating and the object 34 from being arranged.

Figure 10:
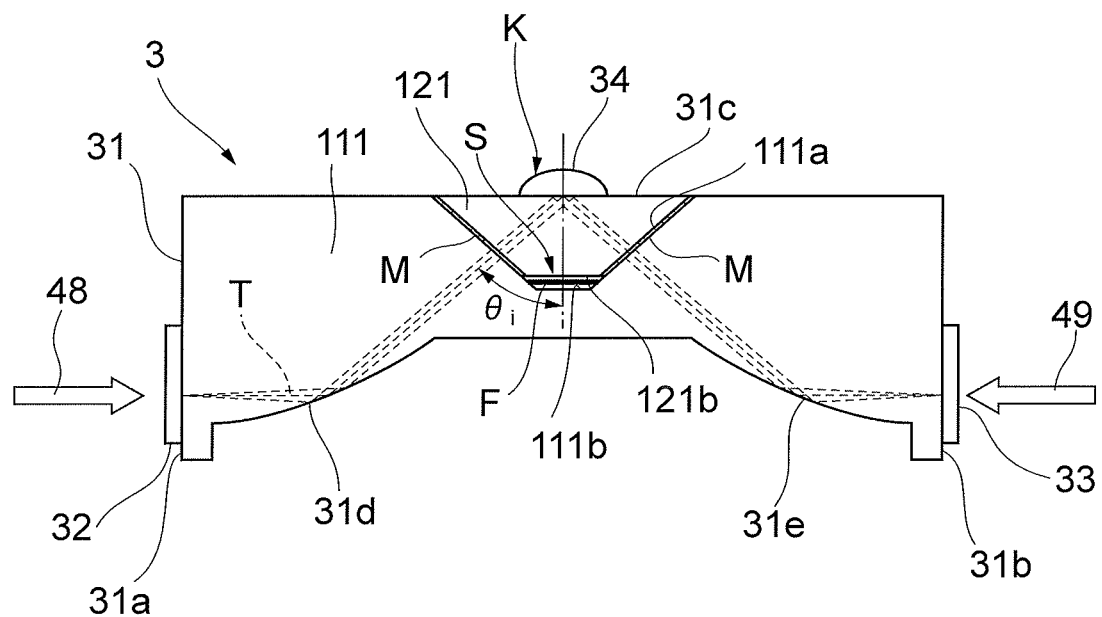
FIG. 10 is a set of diagrams illustrating still another modified example of the first and second prism parts.
Figure 10:
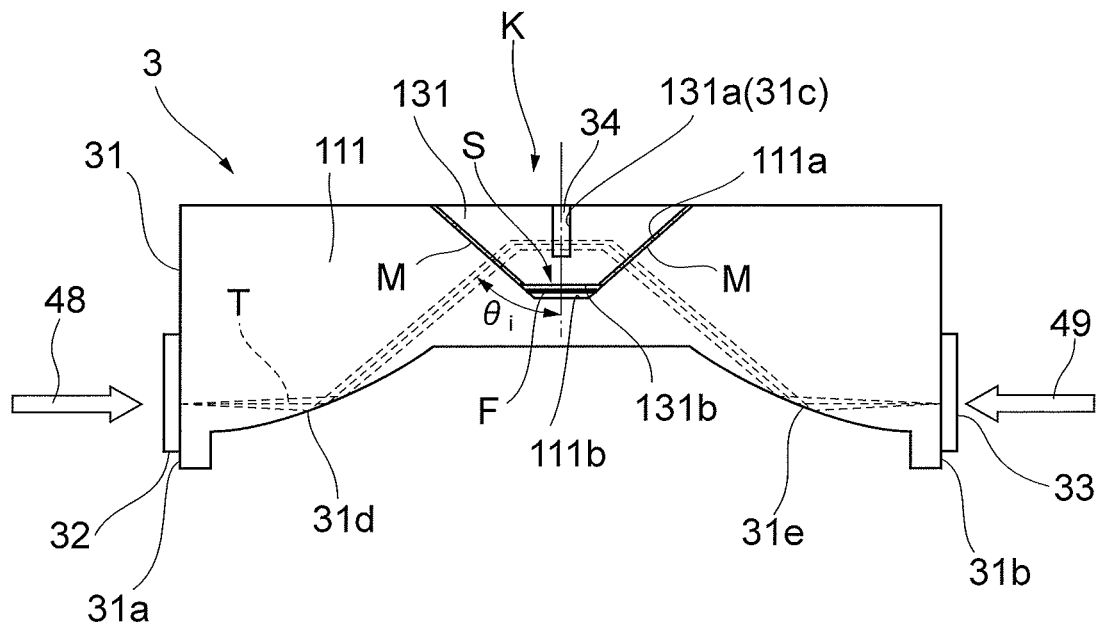

A modified example may be constructed as illustrated in FIGS. 10(a) and 10(b) such that a bottom part of a groove 111a of a main part 111 is formed into a flat surface 111b, while bottom parts of first and second prism parts 121, 131 are formed into flat surfaces 121b, 131b, so as to form spaces S between the flat surfaces 111b, 121b and between the flat surfaces 111b, 131b. This structure can also make it easy to handle the first and second prism parts 121, 131.

Film members F may be disposed in the spaces S such as to protrude out of the mating part between the main part 111 and the first prism part 121 and the mating part between the main part 111 and the second prism part 131. In this case, holding the film members F makes it easy to remove the first and second prism parts 121, 131 from the main part 111. When using the film members F, the spaces S are not always necessary, so that the flat surfaces 111b, 121b may be in contact with the film member F, while the flat surfaces 111b, 131b may be in contact with the film member F.

REFERENCE SIGNS LIST

1 ... terahertz-wave spectrometer; 2 ... laser light source; 3 ... integral prism; 13 ... beam splitter (branching unit); 31 ... spectroscopic prism; 31a ... entrance surface; 31b ... exit surface; 31c ... arrangement surface; 32 ... terahertz-wave generator; 33 ... terahertz-wave detector; 34 ... object to be measured; 48 ... pump light; 49 ... probe light; 51, 81, 111 ... main part (prism member); 51a, 81a, 111a ... depression; 61, 91, 111 ... first prism part; 71, 101, 131 ... second prism part; 91c, 101d ... lug; F ... film member; M ... matching oil; S ... space; T ... terahertz wave

The invention claimed is:

1. A terahertz-wave spectrometer comprising:
a light source for emitting laser light;
a branching unit for splitting the laser light emitted from the light source into pump light and probe light;
a terahertz-wave generator for generating a terahertz wave in response to the pump light incident thereon after branching off at the branching unit;
a spectroscopic prism, having entrance and exit surfaces for the terahertz wave and an arrangement part for an object to be measured, for propagating therewithin the terahertz wave incident on the entrance surface and emitting the terahertz wave from the exit surface; and
a terahertz-wave detector for receiving the terahertz wave emitted from the exit surface of the spectroscopic prism and the probe light branching off at the branching unit and detecting a correlation between the terahertz wave and the probe light;
wherein the spectroscopic prism comprises:
a main part having the entrance and exit surfaces, a depression formed on an upper face side, a first optical surface for collimating or converging the terahertz wave toward the depression, and a second optical surface for converging the terahertz wave having passed through the depression toward the exit surface;
a first prism part, formed by a member having a refractive index substantially equal to that of the main part, including a projection adapted to detachably mate with the depression and having an upper face provided with the arrangement part for the object; and
a second prism part, formed by a member having a refractive index lower than that of the main part, including a projection adapted to detachably mate with the depression and having a groove to become the arrangement part for the object, the groove being formed from an upper face toward a leading end of the projection;
wherein the terahertz wave incident on the entrance surface is transmitted through the depression and reflected by the arrangement part when the first prism part mates with the main part, but is refracted by the depression and transmitted through the groove when the second prism part mates with the main part.

2. A terahertz-wave spectrometer according to claim 1, wherein a matching oil is disposed in each of the mating part between the main part and the first prism part and the mating part between the main part and the second prism part.

3. A terahertz-wave spectrometer according to claim 1, wherein film members are disposed in the mating part between the main part and the first prism part and the mating part between the main part and the second prism part such as to protrude out thereof.

4. A terahertz-wave spectrometer according to claim 1, wherein spaces exist in a part of the mating part between the main part and the first prism part and a part of the mating part between the main part and the second prism part.

5. A terahertz-wave spectrometer according to claim 1, wherein the first and second prism parts are provided with lugs.

6. A prism member used in a terahertz-wave spectrometer comprising:
a light source for emitting laser light;
a branching unit for splitting the laser light emitted from the light source into pump light and probe light;
a terahertz-wave generator for generating a terahertz wave in response to the pump light incident thereon after branching off at the branching unit;
a spectroscopic prism, having entrance and exit surfaces for the terahertz wave and an arrangement part for an object to be measured, for propagating therewithin the terahertz wave incident on the entrance surface and emitting the terahertz wave from the exit surface; and
a terahertz-wave detector for receiving the terahertz wave emitted from the exit surface of the spectroscopic prism and the probe light branching off at the branching unit and detecting a correlation between the terahertz wave and the probe light;
the prism member having:
the entrance and exit surfaces;
a depression formed on an upper face side and adapted to detachably mate with another prism member including the arrangement part for the object; and
a first optical surface for collimating or converging the terahertz wave toward the arrangement part and a second optical surface for converging the terahertz wave from the arrangement part toward the exit surface when the prism part mates with the depression.

* * * * *